(12) United States Patent
Suzuki et al.

(10) Patent No.: US 9,364,423 B2
(45) Date of Patent: Jun. 14, 2016

(54) WHITENING AGENT, ANTI-AGING AGENT, AND ANTIOXIDANT AGENT

(71) Applicant: Shiseido Company, Ltd., Tokyo (JP)

(72) Inventors: Rikako Suzuki, Yokohama (JP); Kiyotaka Hasegawa, Yokohama (JP); Kiyoshi Sato, Yokohama (JP); Tokiya Yokoi, Yokohama (JP); Ken Kusakari, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 385 days.

(21) Appl. No.: 13/954,176

(22) Filed: Jul. 30, 2013

(65) Prior Publication Data

US 2013/0315850 A1    Nov. 28, 2013

Related U.S. Application Data

(62) Division of application No. 13/138,378, filed as application No. PCT/JP2010/000623 on Feb. 3, 2010, now abandoned.

(30) Foreign Application Priority Data

Feb. 9, 2009    (JP) .................................. 2009-027227

(51) Int. Cl.
| | | |
|---|---|---|
| A61K 36/00 | (2006.01) | |
| A61K 8/97 | (2006.01) | |
| A61K 36/11 | (2006.01) | |
| A61Q 19/02 | (2006.01) | |
| A61Q 19/08 | (2006.01) | |

(52) U.S. Cl.
CPC . *A61K 8/97* (2013.01); *A61K 36/11* (2013.01); *A61Q 19/02* (2013.01); *A61Q 19/08* (2013.01)

(58) Field of Classification Search
None
See application file for complete search history.

(56) References Cited

FOREIGN PATENT DOCUMENTS

| | | |
|---|---|---|
| CN | 1739740 A | 3/2006 |
| CN | 101028278 A | 9/2007 |
| JP | 08-133939 A | 5/1996 |
| JP | 09-263534 A | 10/1997 |
| JP | 09263534 A * | 10/1997 |
| JP | 11-501311 A | 2/1999 |
| JP | 2006-347926 A | 12/2006 |
| WO | WO 2008/147022 A1 | 12/2008 |

OTHER PUBLICATIONS

Psilotum from Wikipedia, accessed on Aug. 21, 2013, pp. 1-2.*
Shi et al., "Hyphenated HSCCC-DPPH for Rapid Preparative Isolation and Screening of Antioxidants from *Selaginella moellendorffii*," Chromatographia, Aug. 2008, 68(3/4):173-178.
Takahashi et al., "Chemical Markers of the Psilotaceae," Biochemical Systematics and Ecology, 1990, 18(1):11-12.
Full English translation of CN 1739740 A, Mar. 1, 2006, 6 pages.

* cited by examiner

*Primary Examiner* — Qiuwen Mi
(74) *Attorney, Agent, or Firm* — Foley & Lardner LLP

(57) ABSTRACT

The present invention is directed to an extrace of *Psilotum* spp., as a skin whitening agent. Whitening agents according to the invention exhibit superior effects, for example, by lightening and whitening skin pigmentation, lightening and whitening aging spots, freckles, chloasma, or the like after sunburn. The *Psilotum* spp. extract of the invention has a superior free radical scavenging ability permitting the extract to control skin aging and skin diseases caused by active oxygen (free radicals), while having a high level of safety.

3 Claims, 2 Drawing Sheets

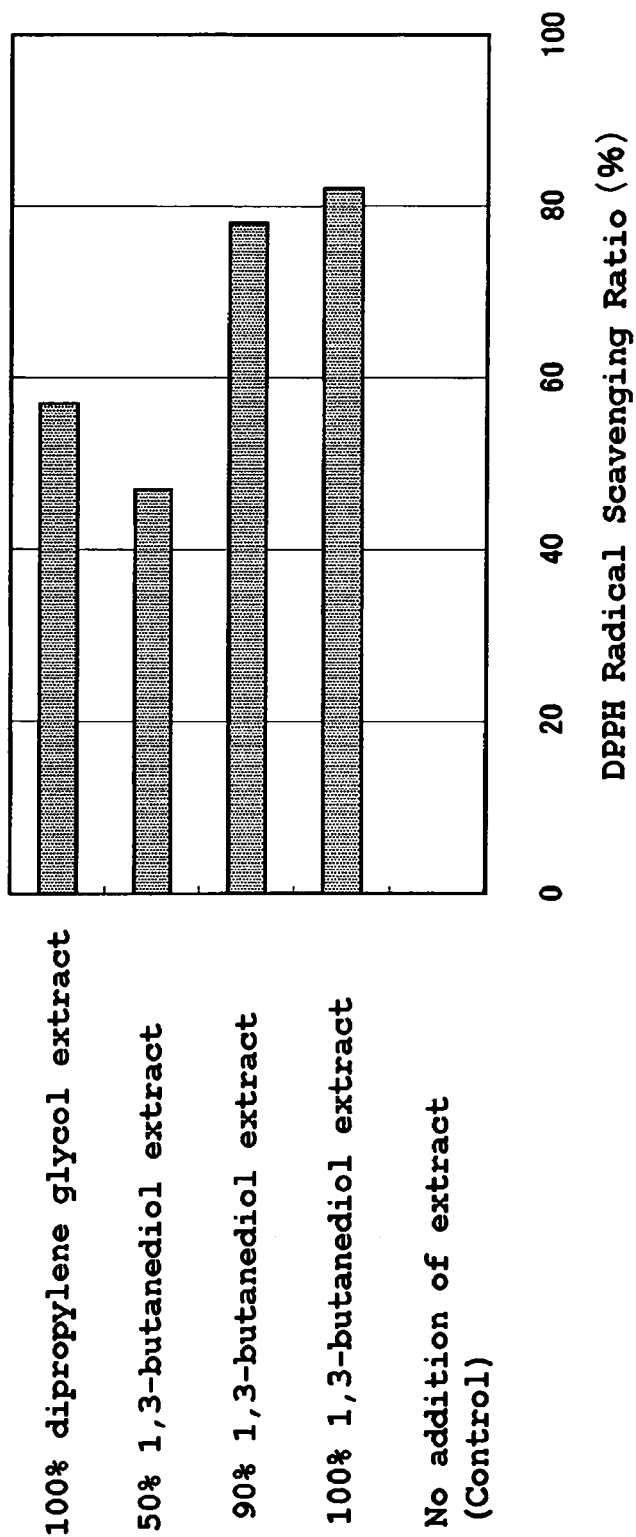

WHITENING AGENT, ANTI-AGING AGENT, AND ANTIOXIDANT AGENT

CROSS-REFERENCE TO RELATED APPLICATIONS

This application is a Divisional of U.S. application Ser. No. 13/138,378, which is the U.S. National Stage application of PCT/JP2010/000623, filed Feb. 3, 2010, which claims priority from Japanese application JP 2009-027227, filed Feb. 9, 2009. The entire contents of each of the aforementioned applications are incorporated herein by reference.

TECHNICAL FIELD

The present invention relates to a whitening agent, an anti-aging agent, and an antioxidant agent, more specifically, relates to a whitening agent, an anti-aging agent, an antioxidant agent comprising a plant extract as an active ingredient, and a skin external preparation comprised thereof.

BACKGROUND ART

While the pathogenesis of aging spots, etc., is partially unknown, it is generally considered that abnormalities of hormones or the stimulation by ultraviolet rays from sunlight causes the formation of melanin pigments and the pigments are abnormally deposited in the skin. The melanin pigments which cause pigmentation of the skin are produced in melanin-producing granules (melanosomes) within melanin cells (melanocytes) between the epidermis and the hypodermis, and the produced melanin diffuses to adjacent cells by osmosis.

The biochemical reaction in melanocytes is presumed to be as follows. Namely, the production process of melanin pigment is that tyrosine, an essential amino acid becomes dopaquinone by the action of the enzyme, tyrosinase, and the dopaquinone is converted to black melanin by enzymatic or non-enzymatic oxidation activity.

Various whitening agents for controlling the occurrence of the aforementioned melanin pigments, comprising extracts derived from plants have been conventionally developed in the anticipation that such extracts are safe and mildly irritating to the skin (refer to, for example, Patent Documents 1 to 4).

However, it is well known that active oxygen is generated by ultraviolet rays. Among active oxygen species, free radical type active oxygen reacts with an oxidizable substrate such as lipid, inducing an oxidation chain reaction. Therefore, active oxygen which can become free radicals amplifies damage to body tissue such as skin.

The skin is always exposed to oxygen and ultraviolet rays, and thus, is the tissue which has the greatest oxidative stress damage by free radicals. Recently, it has been considered that a variety of active oxygen species generated by ultraviolet rays cause the peroxidation of sebum and lipid, protein degeneration, enzyme inhibition, etc., and thereby, the inflammation, etc., of the skin is induced over the short term, and aging, cancer, and the like are caused over a prolonged period of time.

Further, it is considered that active oxygen and peroxidized lipids are associated with skin diseases such as atopic dermatitis, contact dermatitis, and psoriasis. In this way, active oxygen (free radicals) is deeply involved in aging of the skin and skin diseases.

Substances having the ability to scavenge free radicals can control and terminate free radical chain reactions, and correspond to, for example, substances referred to as antioxidant agents.

Therefore, skin external preparations comprising an antioxidant agent are anticipated to have an effect of prevention and improvement of aging in the skin (for example, aging spots, wrinkles, sagging skin, etc.) caused by photooxidative stress. Further, the skin external preparations can be anticipated to have an effect of prevention and improvement, as skin external preparations for various skin diseases associated with free radicals.

Vitamin E and vitamin C which are known as antioxidant agents are in vivo free radicals scavenger antioxidant substances. Further, the synthetic antioxidant substances of BHT and BHA are also known. Furthermore, as conventional antioxidant agents derived from plants, extracts of Chinese mushrooms, enoki mushrooms, shimeji mushrooms, maitake mushrooms, matsutake mushrooms, *Ganoderma lucidum, Daedalea dickinsii, Pholiota nameko*, and other basidiomycetes have been reported (Patent Documents 6 to 8). Furthermore, antioxidant agents consisting of extracts of a plant belonging to the genus *Verbascum* of the family Scrophulariaceae (Patent Document 9) and antioxidant agents consisting of extracts of a plant belonging to the genus *Cordia* of the family Boraginaceae (Patent Document 10) have been reported.

Further, Patent Document 5 mentions a solvent extraction of *Psilotum nudum* belonging to the family Psilotaceae as a plant extract comprising apigenin or amentoflavone. Patent Document 5 shows no data that this plant extract has a melanogenesis stimulation activity, thus, in Patent Document 5, the function of the solvent extraction of *Psilotum nudum* itself is unclear. The present invention relates to the melanogenesis-inhibitory action and the free radical scavenging-type antioxidation activity due to the *Psilotum* extract. Thus, the description of Patent Document 5 and the contents of the present invention are completely different.

PRIOR ART DOCUMENTS

Patent Documents

[Patent Document 1] Japanese Unexamined Patent Publication (Kokai) No. 8-310939
[Patent Document 2] Japanese Unexamined Patent Publication (Kokai) No. 7-89843
[Patent Document 3] Japanese Unexamined Patent Publication (Kokai) No. 9-30954
[Patent Document 4] Japanese Unexamined Patent Publication (Kokai) No. 2003-73224
[Patent Document 5] Japanese Unexamined Patent Publication (Kokai) No. 9-263534
[Patent Document 6] Japanese Unexamined Patent Publication (Kokai) No. 5-317016
[Patent Document 7] Japanese Unexamined Patent Publication (Kokai) No. 6-65575
[Patent Document 8] Japanese Unexamined Patent Publication (Kokai) No. 59-124984
[Patent Document 9] Japanese Unexamined Patent Publication (Kokai) No. 11-171723
[Patent Document 10] Japanese Unexamined Patent Publication (Kokai) No. 11-171720

DISCLOSURE OF THE INVENTION

Problems to be Solved by the Invention

As described above, regarding the whitening agent and the anti-aging agent derived from plants, there is a desire to discover a new plant which brings about new whitening and anti-aging effects. The present invention has been completed in view of such conventional circumstances, and an object of the present invention is to provide a whitening agent, an anti-aging agent, and an antioxidant agent derived from a new plant.

Means of Solving the Problems

The present inventors have performed extensive studies taking the above circumstances into account, and as a result, have found that there is a superior skin whitening activity and antioxidation activity in a specified plant extract, whereby the present invention has been completed.

The present invention is a whitening agent comprising an extract of *Psilotum* spp., the family Psilotaceae.

The present invention is a skin external preparation for whitening, comprising an extract of *Psilotum* spp., the family Psilotaceae.

The present invention is an anti-aging agent comprising an extract of *Psilotum* spp., the family Psilotaceae.

The present invention is a skin external preparation for anti-aging, comprising an extract of *Psilotum* spp., the family Psilotaceae.

The present invention is an antioxidant agent comprising an extract of *Psilotum* spp., the family Psilotaceae.

The present invention is a skin external preparation for antioxidation, comprising an extract of *Psilotum* spp., the family Psilotaceae.

Effect of the Invention

The whitening agent of the present invention has a superior skin whitening activity, has a superior effect in lightening and whitening pigmentation, aging spots, freckles, chloasma, or the like after sunburn.

The anti-aging agent and the antioxidant agent of the present invention have a superior free radical scavenging ability for preventing and controlling aging in the skin and skin diseases caused by active oxygen (free radicals).

The skin external preparation for whitening of the present invention can bring about a superior a whitening effect when applied to the skin, has a superior effect in lightening and whitening pigmentation, aging spots, freckles, chloasma, or the like after sunburn, and has a high level of safety.

The skin external preparation for anti-aging and the skin external preparation for antioxidation of the present invention can bring about a superior free radical scavenging ability when applied to the skin, can prevent and control aging in the skin and skin diseases caused by active oxygen (free radicals), and has a high level of safety.

BRIEF DESCRIPTION OF THE DRAWINGS

[FIG. 2] is a drawing showing the radical elimination method activity of the plant extract of the present invention.

MODE FOR CARRYING OUT THE INVENTION

Figure 1:
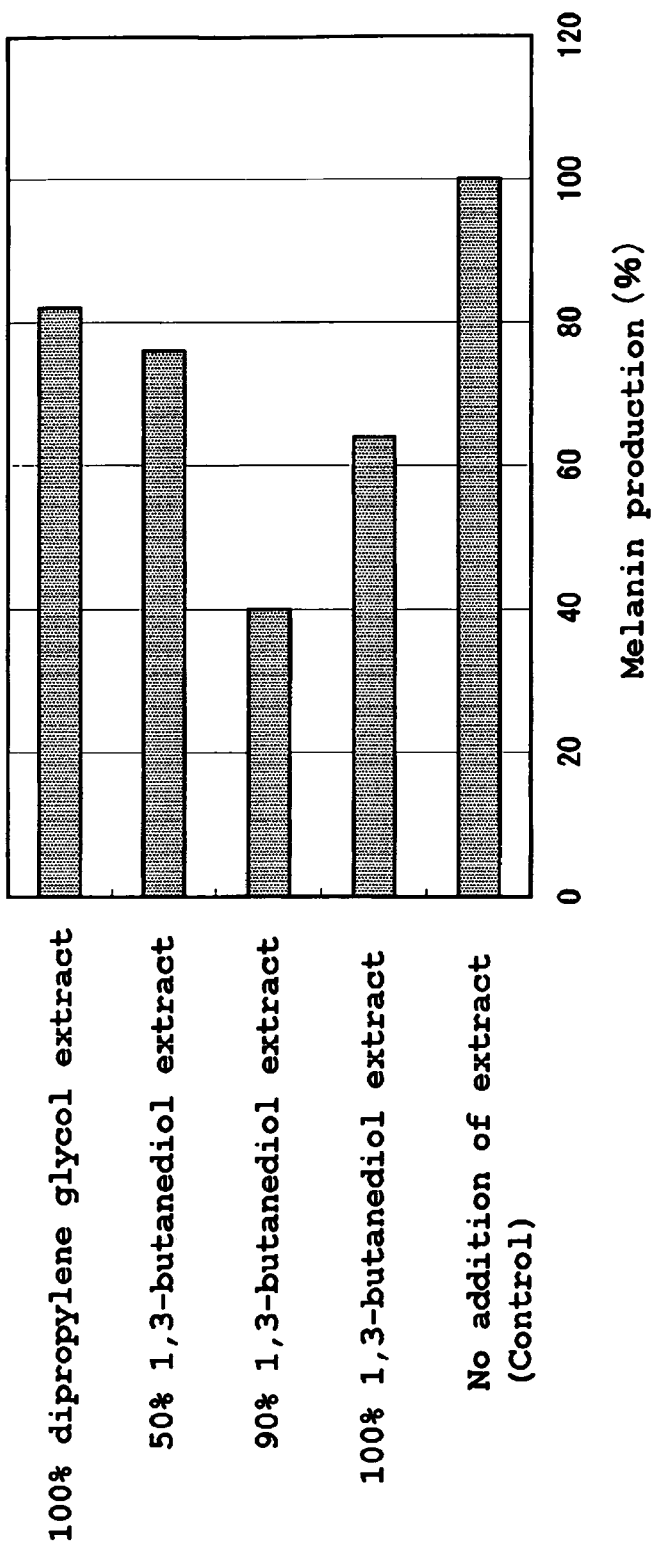
[FIG. 1] is a drawing showing the melanogenesis-inhibitory action of the plant extract of the present invention.

The present invention will be explained below in detail.

The plant used in the present invention is a plant belonging to the family Psilotaceae, the genus *Psilotum*, which is a cohort of pteridophytes. As plants of the genus *Psilotum*, there are known *Psilotum nudum, Psilotum complanatum, Psilotum flabellatum, Psilotum flaccidum, Psilotum triquetrum, Psilotum truncatum,* etc.

As a species which is distributed throughout Japan, *Psilotum nudum* may be mentioned and is widely distributed in sub-central Japan, Taiwan, southern China, Southeast Asia, etc. In the present invention, specifically, *Psilotum nudum* is preferable as a plant belonging to the family Psilotaceae, the genus *Psilotum*.

There had been no reports until the present inventors initially discovered that there is a skin whitening activity, an antioxidant activity, and an anti-aging activity in the plant extract of the present invention.

The extract of the plant of the genus *Psilotum* used in the present invention can be obtained by appropriately drying or crushing the whole plant, followed by extraction with a solvent. The extraction may be performed by standing still at room temperature, or can be accelerated by heating, stirring, and refluxing according to need. The obtained extract may be used directly or used after a treatment such as filtering, concentrating, or decoloring. Further, it is possible to use the extract by removing the solvent followed by the re-dissolution in a different solvent. It is also possible to use the extract by further purifying the extract by charcoal, column chromatography, etc.

As the extraction portion, other than the whole plant, specific portions may be collected for extraction.

The extraction solvent used in the present invention may be any solvent commonly used in extraction. Specifically, alcohol such as methanol, ethanol, 1,3-butanediol, propylene glycol, and dipropylene glycol; aqueous alcohol; an organic solvent such as acetone, ethyl acetate, and chloroform can be used alone or in combination. However, methanol, ethanol, 1,3-butanediol, acetone, etc., are preferable. Further, these extracts may be purified by solvent fractionation, charcoal treatment, column chromatography, etc.

The whitening agent, the antioxidant agent, and the anti-aging agent of the present invention are characterized by comprising the extract of the plant of the genus *Psilotum*, but may comprise other various components unless the effect of the present invention is impaired.

The whitening agent or the anti-aging agent of the present invention may be blended with a skin external preparation to from a skin external preparation for whitening or a skin external preparation for anti-aging on the basis of the antioxidant activity. These skin external preparations can be optimally used in the fields, specifically, cosmetics, pharmaceutical products, quasi drugs, etc.

The amount of the plant extract in the skin external preparation comprising the whitening agent or the anti-aging agent of the present invention, as the dried residue of the components derived from plants of the genus *Psilotum*, is normally 0.00001 mass % or more, preferably, 0.0001 mass % or more. If the amount is too small, the effect cannot be sufficiently brought about. The upper limit is not aspecifically limited unless the effect of the present invention is impaired. However, the excessive addition cannot bring about a remarkable effect appropriate for the increase, and exerts a bad influence in formulation design, usability, etc. Thus, the amount is normally 10 mass % or less, more preferably, 5 mass % or less.

The skin external preparation comprising the whitening agent or the anti-aging agent of the present invention is prepared by blending the whitening agent or the anti-aging agent with a base for external use. Other than the aforementioned essential components, the skin external preparation may appropriately contain, if needed, components used in skin external preparations as, e.g., general cosmetics and pharmaceutical products, for example, moisturizer agents, antioxidants, oil ingredient, ultraviolet rays absorbents, surfactants, thickening agents, alcohols, powder ingredients, coloring materials, aqueous ingredients, water, plant extracts, and various skin nutrients, unless the effect of the present invention is impaired.

In addition, there may be appropriately blended sequestering agents such as disodium edetate, trisodium edetate, sodium citrate, sodium polyphosphate, sodium metaphosphate, and gluconic acid; medicines such as caffeine, tannin, verapamil, tranexamic acid, and their derivatives, licorice extract, glabridin, hot water extracts of the fruit of firethorn, various herbal medicines, tocopherol acetate, glycyrrhizinate, their derivatives, or their salts, other whitening agents such as vitamin C, magnesium ascorbyl phosphate, glucoside ascorbic acid, arbutin, kojic acid, alkoxybenzoic acid and/or their salts; sugars such as glucose, fructose, mannose, sucrose, trehalose, etc.

The skin external preparation comprising the whitening agent or the anti-aging agent of the present invention may be in the form of, for example, an ointment, cream, emulsion, lotion, pack, bath agent, etc., conventional skin external preparations. The form is not particularly limited.

The whitening agent or the anti-aging agent of the present invention may be blended with food, as well as used in the aforementioned preparations for external use. The intake of such food is expected to bring about the whitening effect and the anti-aging effect from inside.

EXAMPLES

The present invention will be further described below with reference to the following examples, but the present invention is not limited to the examples. The amounts are mass % unless specifically indicated.

First, the method of preparation of the plant extract used in the examples, and the testing methods and the results relating to the melanogenesis inhibitory effect and the antioxidant effect will be explained.

1. Preparation of Test Samples

All the plants used in the examples were from Okinawa, but the plant of the present invention is not limited thereto.
(1) 75 ml of methanol was added to 7.4 g of the whole plant of *Psilotum nudum*. Filtration was performed after immersion at room temperature over seven days. The solvent of the filtrate was removed by evaporation in vacuo, and 1.360 g of a dry solid substance was obtained.
(2) 10 ml of a 50% ethanol aqueous solution was added to 1.04 g of the whole plant of *Psilotum nudum*. Filtration was performed after extraction over three days while stirring at room temperature. The solvent of the filtrate was removed by evaporation in vacuo, and 0.18 g of a dry solid substance was obtained.
(3) 10 ml of a 70% ethanol aqueous solution was added to 1.02 g of the whole plant of *Psilotum nudum*. Filtration was performed after extraction over three days while stirring at room temperature. The solvent of the filtrate was removed by evaporation in vacuo, and 0.21 g of a dry solid substance was obtained.
(4) 10 ml of a 90% ethanol aqueous solution was added to 1.03 g of the whole plant of *Psilotum nudum*. Filtration was performed after extraction over three days while stirring at room temperature. The solvent of the filtrate was distilled, and 0.21 g of a dry solid substance was obtained.
(5) 10 ml of 100% ethanol was added to 1.05 g of the whole plant of *Psilotum nudum*. Filtration was performed after extraction over three days while stirring at room temperature. The solvent of the filtrate was removed by evaporation in vacuo, and 0.15 g of a dry solid substance was obtained.
(6) 10 ml of acetone was added to 1.00 g of the whole plant of *Psilotum nudum*. Filtration was performed after extraction over three days while stirring at room temperature. The solvent of the filtrate was removed by evaporation in vacuo, and 0.072 g of a dry solid substance was obtained.
(7) 10 ml of ethyl acetate was added to 1.01 g of the whole plant of *Psilotum nudum*. Filtration was performed after extraction over three days while stirring at room temperature. The solvent of the filtrate was removed by evaporation in vacuo, and 0.067 g of a dry solid substance was obtained.
(8) 10 ml of 1,3-butanediol was added to 1.00 g of the whole plant of *Psilotum nudum*. Filtration was performed after extraction over three days while stirring at room temperature. The evaporation residue (105° C., under reduced pressure for six hours) of the extract was measured to be 6.3 mg/g.
(9) 10 ml of dipropylene glycol was added to 1.00 g of the whole plant of *Psilotum nudum*. Filtration was performed after extraction over three days while stirring at room temperature. The evaporation residue (105° C., under reduced pressure for six hours) of the extract was measured to be 5.3 mg/g.
(10) 1.0 g of the dry solid substance obtained in (1) was dispersed and dissolved in 50 ml of water, and then, extracted three times with 50 ml of ethyl acetate. The ethyl acetate phase was concentrated and 272 mg of a dried substance was obtained. The product was dissolved in acetone. Filtration was performed after charcoal treatment. The filtrate was concentrated and 201 mg of the discolored substance was obtained (ethyl acetate fractionation).

2. Evaluation of Melanogenesis Inhibitory Effect (Method and Results)

The *Psilotum nudum* extracts obtained by the respective extraction methods were used as test samples, and the melanogenesis inhibitory effect was measured and evaluated by the following method.

(1) Cell Seeding and the Addition of Testing Substances

Mouse B16 melanoma cells were seeded in 6-well plates at 100,000 cells/well. The following day, the test sample (in the case of a dried substance, solvent: DMSO) was added.

(2) Cell Proliferation Test

The culture medium was removed three days after the addition of the test sample, and subsequently, 1 ml of EMEM culture medium containing 10% alamar blue solution was added to the culture. After incubation at 37° C. for 30 minutes, 100 μl of the medium was transferred to a 96-well plate, and the fluorescence was measured at a wavelength of 590 nm using an excitation wavelength of 544 nm. Cell numbers were expressed as relative values to that of the control (only the solvent containing no plant extract added) by comparing the fluorescence intensities, which reflect the number of viable cells.

The larger cell number indicates the lower toxicity of a test sample. If the cell number of a test sample was less 80%, the sample was considered as "cytotoxic".

(3) Determination of Melanin Amount

After the removal of the culture medium by aspiration, the cells were washed with a buffer (phosphate buffer solution 50 mM, pH 6.8), and subsequently, lysed by adding 1 M NaOH, and the absorbance at 475 nm was measured. Melanin amounts were expressed as relative values to that of the control (only the solvent containing no plant extract added) by comparing the absorbances, which reflect melanin amounts. The lower melanin amount indicates the higher effect on melanogenesis inhibition.

Melanogenesis inhibitory effects for the respective plant extracts are shown in Table 1. The concentrations of *Psilotum nudum* extracts were shown as dried extract concentration unless otherwise stated.

TABLE 1

| Psilotum nudum extraction sample | 0 ppm Melanin amount | 0 ppm Cell number | 0.3 ppm Melanin amount | 0.3 ppm Cell number | 1 ppm Melanin amount | 1 ppm Cell number | 3 ppm Melanin amount | 3 ppm Cell number | 10 ppm Melanin amount | 10 ppm Cell number |
|---|---|---|---|---|---|---|---|---|---|---|
| Methanol extract | 100 | 100 | 87 | 96 | 80 | 97 | 49 | 104 | 18 | 87 |
| 100% ethanol extract | 100 | 100 | 109 | 98 | 99 | 102 | 95 | 99 | 53 | 110 |
| 90% ethanol extract | 100 | 100 | 100 | 98 | 98 | 99 | 85 | 106 | 47 | 112 |
| 50% ethanol extract | 100 | 100 | 106 | 101 | 97 | 102 | 97 | 105 | 67 | 107 |
| Acetone extract | 100 | 100 | 95 | 100 | 90 | 99 | 68 | 103 | 30 | 93 |

From FIG. 1, it is understood that the plant extracts used in the present invention have a superior melanin inhibitory activity and are useful as whitening agents. Numerous solvent extracts other than those shown in Table 1 were evaluated, and a high whitening effect was observed as shown in FIG. 1. FIG. 1 shows the results when the respective solvent extracts were adjusted to a final concentration of 0.04% (volume/volume). In each case, cytotoxicity was not found. Note that, regarding the control, each solvent alone was similarly adjusted to 0.04% (volume/volume).

Furthermore, it is understood from Table 2 that the ethyl acetate fractionate of the methanol extract also showed a high whitening effect.

TABLE 2

| Psilotum nudum extraction sample | 0 ppm Melanin amount | 0 ppm Cell number | 0.3 ppm Melanin amount | 0.3 ppm Cell number | 1 ppm Melanin amount | 1 ppm Cell number | 3 ppm Melanin amount | 3 ppm Cell number | 10 ppm Melanin amount | 10 ppm Cell number |
|---|---|---|---|---|---|---|---|---|---|---|
| Ethyl acetate fractionation of the methanol extract | 100 | 100 | 97 | 101 | 87 | 102 | 59 | 102 | 21 | 97 |

As described above, it is understood that the plant extracts used in the present invention have a superior melanogenesis inhibitory action, and are useful as whitening agents.

3. Evaluation and Results of the Antioxidant Effect

The *Psilotum nudum* extracts obtained by the respective extraction methods were used as the test samples, and the antioxidant effect was measured and evaluated by the following method.

(1) Evaluation Method of Antioxidant Effect (DPPH Radical Quenching Assay)

The test substance dissolved in dimethyl sulfoxide was injected into a 96-well plate at 10 μl/well, and subsequently, 1 mmol/l of 1,1-diphenyl-2-picrylhydrazyl solution was added thereto at 90 μl/well. After leaving at room temperature for ten minutes, the absorbency at 517 nm was determined, and the scavenging ratio (%) of radicals to the amount in the control was obtained from the data of the absorbency. The evaluation results are shown in Table 3.

TABLE 3

| | DPPH radical scavenging ratio (%) | | | | | | |
|---|---|---|---|---|---|---|---|
| Psilotum nudum extract sample | Concentration | | | | | | |
| | 0 ppm | 10 ppm | 30 ppm | 100 ppm | 300 ppm | 1000 ppm | 2000 ppm |
| 50% ethanol extract | 0 | 0 | 2 | 11 | 41 | 82 | 89 |
| 70% ethanol extract | 0 | 3 | 7 | 23 | 57 | 92 | 88 |
| 90% ethanol extract | 0 | 6 | 17 | 43 | 81 | 78 | 75 |

TABLE 3-continued

| | DPPH radical scavenging ratio (%) | | | | | | |
|---|---|---|---|---|---|---|---|
| Psilotum nudum | Concentration | | | | | | |
| extract sample | 0 ppm | 10 ppm | 30 ppm | 100 ppm | 300 ppm | 1000 ppm | 2000 ppm |
| 100% ethanol extract | 0 | 12 | 23 | 53 | 80 | 73 | 68 |
| Acetone extract | 0 | 9 | 32 | 78 | 78 | 72 | 61 |
| Ethyl acetate extract | 0 | 13 | 31 | 77 | 79 | 76 | 61 |

From Table 3, it is understood that, regarding the plant extracts used in the present invention, the respective solvent extracts have superior radical scavenging activities, and are useful as antioxidant agents. Numerous solvent extracts other than in Table 3 were evaluated, a high antioxidant effect as shown in FIG. 2 was observed in the extract extracted with polyols such as 1,3-butanediol and dipropylene glycol. FIG. 2 shows the results when each solvent extract was adjusted to a final concentration of 1% (volume/volume). In each case, cytotoxicity was not found.

From the above stated results, the extracts of the plant of the genus Psilotum of the present invention show a superior antioxidant effect, and thus, bring about a superior antioxidant activity for human skin. Therefore, the plant extract, if blended with an external use agent, can be used as an anti-aging agent for preventing the aging of skin and maintaining the condition of youthful and healthy skin.

Below, the application examples of the whitening agent and the anti-aging agent in the various forms of the present invention are explained as blending formulation examples. The present invention is not limited to these formulation examples, and is, needless to say, specified by the claims.

The Psilotum nudum extract amount in each formulation is shown as the amount of dry residue after removal of the extraction solvent.

| Blending formulation example 1 (Lotion) | mass % |
|---|---|
| trimethylglycine | 1.0 |
| Psilotum nudum ethanol extract | 0.00001 |
| glycerin | 1.0 |
| 1,3-butylene glycol | 5.0 |
| sodium alginate | 0.1 |
| ethyl alcohol | 5.0 |
| polyoxyethylene polyoxypropylene decyltetradecylether | 0.2 |
| sodium hexametaphosphate | q.s. |
| citric acid | q.s. |
| sodium citrate | q.s. |
| phenoxyethanol | q.s. |
| fragrance | q.s. |
| purified water | balance |

| Blending formulation example 2 (Lotion) | mass % |
|---|---|
| Psilotum nudum acetone extract, 1,3-butanediol redissolved extract | 5.0 |
| glycerin | 2.0 |
| 1,3-butylene glycol | 4.0 |
| polyoxyethylene methyl glucoside | 1.0 |
| PEG/PPG-14/7 dimethyl ether | 3.0 |
| erythritol | 1.0 |
| polyoxyethylene hydrogenated castor oil | 0.5 |
| polyglyceryl diisostearate | 0.3 |
| triethylhexanoin | 0.3 |
| trisodium EDTA | q.s. |
| citric acid | q.s. |
| sodium citrate | q.s. |
| phenoxyethanol | q.s. |
| purified water | balance |

| Blending formulation example 3 (lotion) | mass % |
|---|---|
| tranexamic acid | 1.0 |
| potassium 4-methoxysalicylate | 1.0 |
| lipoic acid | 0.1 |
| Hamamelis leaf extract | 0.1 |
| hypotaurine | 0.1 |
| Sophora flavescens extract | 0.1 |
| Prunus perscia extract | 0.1 |
| Beech bud extract | 0.1 |
| Psilotum nudum 1,3-butanediol extract | 0.0001 |
| magnesium ascorbyl phosphate | 0.1 |
| thiotaurine | 0.1 |
| green tea extract | 0.1 |
| peppermint extract | 0.1 |
| Iris florentina root extract | 1.0 |
| trimethylglycine | 1.0 |
| glycerin | 1.0 |
| 1,3-butylene glycol | 5.0 |
| hydroxyethyl cellulose | 0.05 |
| ethyl alcohol | 5.0 |
| polyoxyethylene polyoxypropylene decyltetradecylether | 0.2 |
| trisodium EDTA | q.s. |
| citric acid | q.s. |
| sodium citrate | q.s. |
| phenoxyethanol | q.s. |
| fragrance | q.s. |
| purified water | balance |

| Blending formulation example 5 (emulsion) | mass % |
|---|---|
| dipotassium glycyrrhizinate | 0.05 |
| tocopherol acetate | 0.5 |
| Psilotum nudum, dipropylene glycol extract | 0.001 |
| sodium L-glutamate | 0.05 |
| fennel extract | 0.1 |
| yeast extract | 0.1 |
| Rehmannia chinensis root extract | 0.1 |
| hydroxypropyl-β-cyclodextrin | 0.1 |
| glycerin | 6.0 |
| 1,3-butylene glycol | 5.0 |
| polyoxyethylene methyl glucoside | 3.0 |
| sunflower seed oil | 1.0 |
| squalene | 2.0 |
| isododecane | 4.0 |
| dimethylpolysiloxane | 3.0 |
| xanthane gum | 0.1 |
| carboxyvinyl polymer | 0.1 |
| acrylic acid-alkyl methacrylate copolymer | 0.1 |
| ethyl alcohol | 5.0 |
| potassium hydroxide | q.s. |
| sodium hexametaphosphate | q.s. |

| Blending formulation example 5 (emulsion) | mass % |
|---|---|
| red iron oxide | q.s. |
| yellow iron oxide | q.s. |
| ethyl paraben | q.s. |
| fragrance | q.s. |
| purified water | balance |

| Blending formulation example 6 (Daily use emulsion) | mass % |
|---|---|
| sodium glycyrrhizinate | 0.1 |
| *Psilotum nudum* acetone extract, ethanol redissolved extract | 0.00003 |
| tocopherol acetate | 0.1 |
| 1,3-butylene glycol | 5.0 |
| squalene | 0.5 |
| isododecane | 10.0 |
| isohexadecane | 25.0 |
| dimethylpolysiloxane | 2.0 |
| polyoxyethylene-methylpolysiloxane copolymer | 1.5 |
| trimethyl siloxysilicate | 1.0 |
| 4-t-butyl-4'-methoxydibenzoylmethane | 1.0 |
| paramethoxy cinnaminic acid 2-ethylhexyl | 5.0 |
| diparamethoxy cinnamic acid mono-2-glyceryl ethylhexanoate | 1.0 |
| silicone coated fine particle titanium oxide | 4.0 |
| dimethyl distearylammonium hectorite | 0.5 |
| spherical polyethylene powder | 3.0 |
| talc | 5.0 |
| trisodium EDTA | q.s. |
| phenoxyethanol | q.s. |
| fragrance | q.s. |
| purified water | balance |

| Blending formulation example 7 (emulsion) | mass % |
|---|---|
| L-arginine | 0.1 |
| royal jelly extract | 0.1 |
| yeast extract | 0.1 |
| *Psilotum nudum* 90% ethanol extract | 10.0 |
| stearyl glycyrrhetinate | 0.05 |
| tocopherol acetate | 0.1 |
| sodium acetylated hyaluronate | 0.1 |
| glycerin | 5.0 |
| dipropylene glycol | 7.0 |
| polyethylene glycol 1500 | 2.0 |
| liquid paraffin | 7.0 |
| vaseline | 3.0 |
| behenyl alcohol | 1.0 |
| batyl alcohol | 2.0 |
| jojoba oil | 1.0 |
| stearic acid | 0.5 |
| isostearic acid | 0.5 |
| behenic acid | 0.5 |
| pentaerythritol tetra 2-ethylhexanoate | 3.0 |
| 2-cetyl ethylhexanoate | 3.0 |
| glycerin monostearate | 1.0 |
| polyoxyethylene glycerin monostearate | 1.0 |
| carboxyvinyl polymer | 0.15 |
| sodium hexametaphosphate | q.s. |
| potassium hydroxide | q.s. |
| methylparaben | q.s. |
| fragrance | q.s. |
| purified water | balance |

| Blending formulation example 8 (emulsion) | mass % |
|---|---|
| glucoside ascorbic acid | 1.5 |
| tranexamic acid | 1.0 |
| tocopherol acetate | 0.1 |
| sodium hyaluronate | 0.05 |
| *Psilotum nudum* 1,3-butanediol extract | 0.0003 |
| pantothenyl ethyl ether | 0.1 |
| stearyl glycyrrhetinate | 0.1 |
| glycerin | 7.0 |
| 1,3-butylene glycol | 5.0 |
| polyethylene glycol 20000 | 0.5 |
| vaseline | 2.0 |
| jojoba oil | 3.0 |
| squalene | 2.0 |
| phytosteryl hydroxystearate | 0.5 |
| behenyl alcohol | 0.5 |
| batyl alcohol | 0.2 |
| dimethylpolysiloxane | 2.0 |
| pentaerythritol tetra 2-ethylhexanoate | 0.1 |
| polyoxyethylene hydrogenated castor oil | 1.0 |
| polyoxyethylene glycerin isostearate | 3.0 |
| 4-t-buytl-4'-methoxydibenzoylmethane | 0.1 |
| diparamethoxy cinnamic acid mono 2-glyceryl ethylhexanoate | 0.1 |
| xanthane gum | 0.1 |
| carboxyvinyl polymer | 0.2 |
| ethanol | 5.0 |
| potassium hydroxide | q.s. |
| sodium pyrosulfite | q.s. |
| sodium hexametaphosphate | q.s. |
| trisodium EDTA | q.s. |
| yellow iron oxide | q.s. |
| paraoxy benzoate ester | q.s. |
| purified water | balance |

| Blending formulation example 9 (cream) | mass % |
|---|---|
| *Psilotum nudum* 90% 1,3-butanediol extract | 0.05 |
| potassium 4-methoxysalicylate | 3.0 |
| propylene glycol | 5.0 |
| glycerin | 8.0 |
| stearic acid | 2.0 |
| stearyl alcohol | 7.0 |
| hydrogenated lanolin | 2.0 |
| squalene | 5.0 |
| 2-octyldodecyl alcohol | 6.0 |
| polyoxyethylene cetyl alcohol ether | 3.0 |
| glycerin monostearate ester | 2.0 |
| potassium hydroxide | q.s. |
| ethyl paraben | q.s. |
| fragrance | q.s. |
| ion-exchange water | balance |

| Blending formulation example 10 (cream) | mass % |
|---|---|
| potassium 4-methoxysalicylate | 1.0 |
| 3-O-ethyl ascorbic acid | 1.0 |
| *Psilotum nudum* 50% ethanol extract | 0.3 |
| Coenxyme Q10 | 0.03 |
| tranexamic acid | 2.0 |
| tocopherol acetate | 0.1 |
| sodium hyaluronate | 0.05 |
| pantothenyl ethyl ether | 0.1 |
| stearyl glycyrrhetinate | 0.1 |
| glycerin | 7.0 |
| 1,3-butylene glycol | 5.0 |
| polyethylene glycol 20000 | 0.5 |
| vaseline | 2.0 |
| behenyl alcohol | 0.5 |
| batyl alcohol | 0.2 |
| squalene | 2.0 |
| phytosteryl hydroxystearate | 0.5 |
| jojoba oil | 3.0 |
| pentaerythritol tetra 2-ethylhexanoate | 1.0 |

| Blending formulation example 10 (cream) | mass % |
|---|---|
| dimethylpolysiloxane | 2.0 |
| polyoxyethylene glycerin isostearate | 1.5 |
| polyoxyethylene hydrogenated castor oil | 1.0 |
| carboxyvinyl polymer | 0.2 |
| xanthane gum | 0.1 |
| ethanol | 5.0 |
| sodium hexametaphosphate | q.s. |
| yellow iron oxide | q.s. |
| trisodium EDTA | q.s. |
| potassium hydroxide | q.s. |
| paraoxy benzoate ester | q.s. |
| purified water | balance |

| Blending formulation example 11 (Two-layer type daytime use emulsion) | mass % |
|---|---|
| tranexamic acid | 2.0 |
| potassium 4-methoxysalicylate | 1.0 |
| *Psilotum nudum* 50% 1,3-butanediol extract | 3.0 |
| dipotassium glycyrrhizinate | 0.02 |
| glutathione | 1.0 |
| thiotaurine | 0.05 |
| sophora flavescens extract | 1.0 |
| dipropylene glycol | 5.0 |
| dimethylpolysiloxane | 5.0 |
| isohexadecane | 25.0 |
| polyoxyethylene-methylpolysiloxane copolymer | 2.0 |
| dimethyl distearylammonium hectorite | 0.5 |
| butyl ethyl propanediol | 0.5 |
| paramethoxy cinnaminic acid 2-ethylhexyl | 7.5 |
| trimethyl siloxysilicate | 5.0 |
| spherical alkyl polyacrylate powder | 5.0 |
| dextrin palmitate coated fine particle zinc oxide | 15.0 |
| trisodium EDTA | q.s. |
| methylparaben | q.s. |
| phenoxyethanol | q.s. |
| fragrance | q.s. |
| purified water | balance |

| Blending formulation example 12 (gel) | mass % |
|---|---|
| potassium 4-methoxysalicylate | 0.1 |
| Lamium album extract | 0.1 |
| *Psilotum nudum* ethyl acetate fractionation dry matter | 0.00001 |
| dipotassium glycyrrhizinate | 0.1 |
| glucoside ascorbic acid | 2.0 |
| tocopherol acetate | 0.1 |
| *Scutellaria baicalensis* extract | 0.1 |
| saxifrage extract | 0.1 |
| glycerin | 2.0 |
| 1,3-butylene glycol | 5.0 |
| polyethylene glycol 1500 | 3.0 |
| polyethylene glycol 20000 | 3.0 |
| agar powder | 1.5 |
| xanthane gum | 0.3 |
| acrylic acid-alkyl methacrylate copolymer | 0.05 |
| cetyl octanoate | 3.0 |
| dimethylpolysiloxane | 5.0 |
| sodium hexametaphosphate | q.s. |
| dibutyl hydroxytoluene | q.s. |
| yellow iron oxide | q.s. |
| citric acid | q.s. |
| sodium citrate | q.s. |
| sodium hydroxide | q.s. |
| phenoxyethanol | q.s. |
| fragrance | q.s. |
| purified water | balance |

The invention claimed is:

1. A method for whitening skin of a subject in need thereof, comprising applying a whitening agent comprising a solvent extract of *Psilotum* spp., the family *Psilotaceae* to the skin.

2. The method for whitening skin according to claim 1, wherein the solvent is selected from the group consisting of aqueous and non-aqueous methanol, ethanol, 1,3-butanediol, propylene glycol, dipropylene glycol, acetone, ethyl acetate, chloroform and combinations thereof.

3. The method for whitening skin according to claim 1, wherein the *Psilotum* spp. is *Psilotum nudum*.

\* \* \* \* \*